(12) United States Patent  (10) Patent No.: US 8,518,246 B2
Lendenfeld  (45) Date of Patent: Aug. 27, 2013

(54) DEVICE FOR MONITORING WATER FOR MICROBIAL GERMS

(75) Inventor: Thomas Lendenfeld, St. Polten (AT)

(73) Assignee: mbOnline GmbH, Krems (AT)

(*) Notice: Subject to any disclaimer, the term of this patent is extended or adjusted under 35 U.S.C. 154(b) by 683 days.

(21) Appl. No.: 12/667,311

(22) PCT Filed: Jul. 2, 2008

(86) PCT No.: PCT/AT2008/000238
§ 371 (c)(1),
(2), (4) Date: Dec. 30, 2009

(87) PCT Pub. No.: WO2009/006657
PCT Pub. Date: Jan. 15, 2009

(65) Prior Publication Data
US 2010/0193413 A1    Aug. 5, 2010

(30) Foreign Application Priority Data

Jul. 9, 2007  (AT) ................. A 1056/2007

(51) Int. Cl.
*B01D 17/12* (2006.01)
*B01D 35/18* (2006.01)
*C12M 1/02* (2006.01)
*C12M 1/12* (2006.01)
*C12M 1/34* (2006.01)

(52) U.S. Cl.
USPC ............ 210/85; 210/96.1; 210/120; 210/134; 210/175; 210/184; 210/198.1; 210/257.1; 210/359; 210/436; 422/513; 422/534; 435/287.1; 435/287.3; 435/289.1; 435/297.1

(58) Field of Classification Search
USPC ............... 73/863.01, 863.02, 863.23, 863.24; 210/85, 90, 96.1, 120, 134, 137, 184, 198.2, 210/258, 406, 407, 409, 418, 87, 175, 198.1, 257.1, 188, 359, 436, 498; 435/4, 5, 287.1, 435/287.3, 289.1, 297.1, 307.1, 308.1; 422/501, 422/509, 513, 527, 534, 105–112, 82.05, 422/82.09, 198, 224, 236, 237
See application file for complete search history.

(56) References Cited

U.S. PATENT DOCUMENTS 3,838,034 A * 9/1974 Groves .................... 204/403.05
4,170,520 A * 10/1979 Weaver ..................... 435/287.1
(Continued)

FOREIGN PATENT DOCUMENTS
DE  8623413  2/1987
EP  0304406  2/1989
(Continued)

OTHER PUBLICATIONS

International Search Report, mailed Oct. 15, 2008, completed by EPO.

*Primary Examiner* — Joseph Drodge
(74) *Attorney, Agent, or Firm* — Design IP

(57) ABSTRACT

A device for continuously, periodically monitoring water for microbial germs, comprising a reactor and at least one reagent feed line into the reactor and at least one metering device for reagents as well as at least one measuring device for detecting the presence of microorganisms, wherein the reactor comprises a reactor chamber and a filtrate chamber, which is separated from said reactor chamber by means of a filter, a water feed line as well as a reagent feed line empty into the reactor chamber and at least one water discharge line leads out of the filtrate chamber, and a controller is set up to use pump/valve means to lead a predefinable quantity of water into the reactor chamber and through the filter as well as to introduce a predefinable quantity of reagent into the reactor chamber.

21 Claims, 7 Drawing Sheets

(56) References Cited

U.S. PATENT DOCUMENTS

Figure 1:
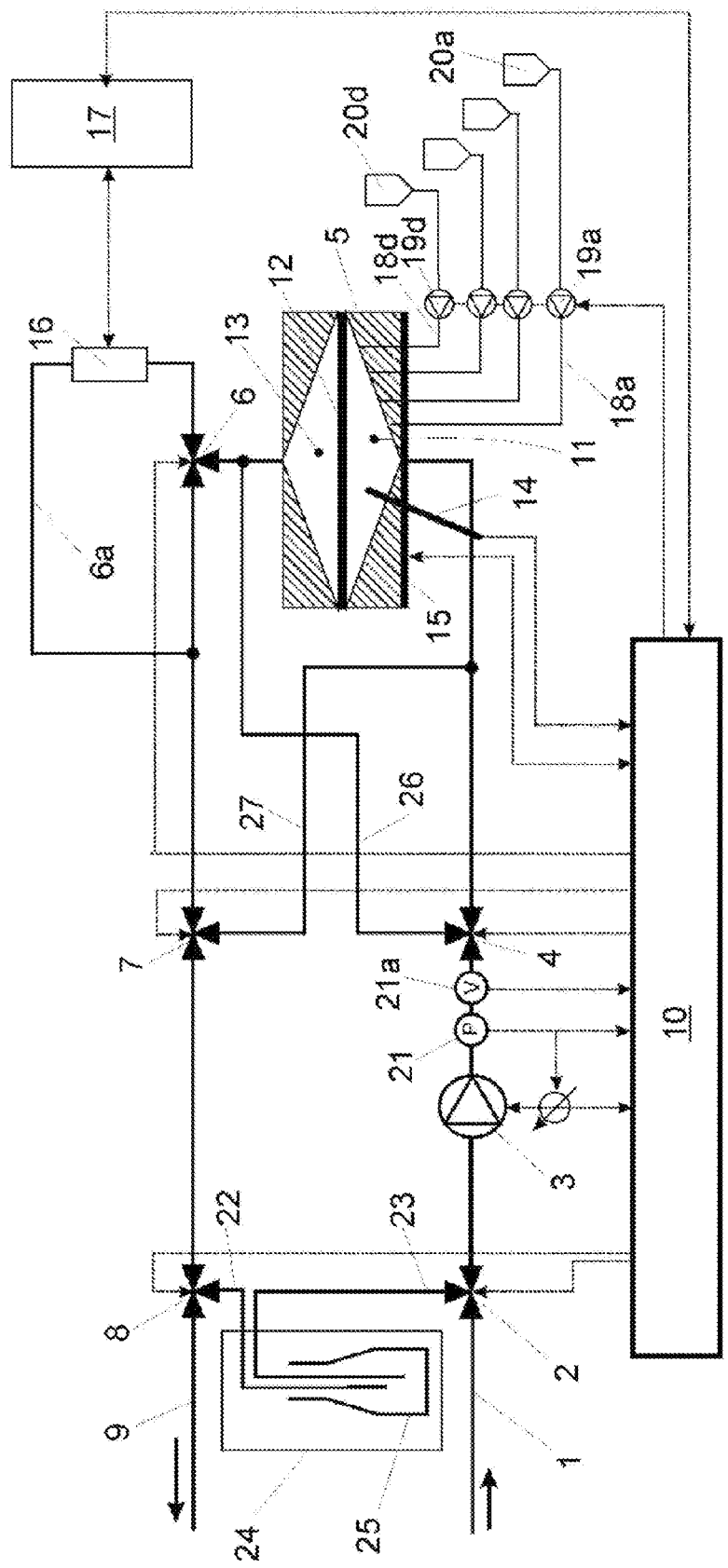

| | | | |
|---|---|---|---|
| 4,229,300 A * | 10/1980 | Benes et al. | 210/96.1 |
| 4,293,309 A * | 10/1981 | Miller | 435/9 |
| 4,345,996 A * | 8/1982 | Lindman et al. | 210/96.1 |
| 4,613,434 A | 9/1986 | Maatta | |
| 5,045,193 A * | 9/1991 | Pinon et al. | 210/232 |
| 5,160,604 A * | 11/1992 | Nakamura et al. | 204/403.06 |
| 5,646,863 A * | 7/1997 | Morton | 702/23 |
| 5,709,840 A * | 1/1998 | Juranas | 422/534 |
| 5,993,742 A * | 11/1999 | Binz et al. | 422/81 |
| 6,245,224 B1 | 6/2001 | Enoki et al. | |
| 6,564,655 B1 * | 5/2003 | Austen et al. | 73/863.02 |
| 6,818,185 B1 | 11/2004 | Petersen et al. | |
| 6,936,156 B2 * | 8/2005 | Smith et al. | 205/775 |
| 7,341,669 B2 * | 3/2008 | Ferguson | 210/741 |
| 2001/0011642 A1 * | 8/2001 | Fukunaga et al. | 210/85 |
| 2003/0116508 A1 * | 6/2003 | Ballreich et al. | 210/739 |
| 2005/0029181 A1 * | 2/2005 | Bell | 210/198.2 |
| 2005/0260569 A1 * | 11/2005 | Houde et al. | 435/5 |
| 2007/0003997 A1 | 1/2007 | Kemmochi et al. | |
| 2008/0063565 A1 * | 3/2008 | Prieto Barranco et al. | 422/68.1 |
| 2010/0133204 A1 * | 6/2010 | Tehrani et al. | 210/785 |

FOREIGN PATENT DOCUMENTS

| | | |
|---|---|---|
| GB | 2365122 | 2/2002 |
| JP | 2003079397 | 3/2003 |

* cited by examiner

DEVICE FOR MONITORING WATER FOR MICROBIAL GERMS

The invention relates to a device for continuously, periodically monitoring water for microbial germs, comprising a reactor, at least one water feed line for the water to be analyzed into the reactor, at least one water discharge line out of the reactor chamber, at least one reagent feed line into the reactor and at least one metering device for reagents, at least one measuring device for detecting the presence of microorganisms and/or the metabolism products thereof, comprising pump/valve means in the feed/discharge lines of the reactor as well as comprising a controller for the programmed controlling of at least the pump/valve means.

In context with the invention, the term "water" defines any type of fluid, the main component of which is water, for example potable water, mineral water, water used for producing potable water, river and sea water, technical process water, e.g. cooling water, circulating water, bio-technological process solutions, e.g. fermentation solutions, sewage and cleaned sewage etc. and food, the main component of which is water, e.g. milk and milk products or products of the beverage industry.

In the case of such waters, it is often desirable or it is also required because of legal regulations, to be able to detect even small stresses caused by microorganisms, wherein the detection of *E. coli* is mentioned as an example herein.

For quite some time, attempts have been made to create methods and devices, which, on the one hand, make it possible to detect even the smallest stresses and which, on the other hand, allow for such a detection within the shortest possible time, so that a virtually continuous water analysis is possible.

The mentioned problem can also be found in document DE 86 23 413 U1. This document discloses a measuring device for detecting coliform bacteria in samples of water, in the case of which hydrogen produced by the bacteria is detected. The measuring device uses one or several closed incubation containers, into which the water to be analyzed, a culture medium and a disinfectant (chlorine water) for cleaning purposes can be introduced. The starting point of this known measuring device is the view that a pre-concentration of bacteria is not desirable for many reasons, in particular because filters may clog and the bacteria concentration at the filter could become too high and because the pre-concentration on the filter membrane is furthermore supposedly irreversible. This would have the result that the use of a filter membrane would make a simple automation impossible.

Another, virtually continuously operating device becomes evident from JP 2003079397. Here, the sample to be analyzed is pumped into a mixing chamber by means of a pump via an intermediate container, a three-way valve and a further pump and reagents are pumped into the mixing chamber by means of valves and a pump. From here, the sample reaches into an incubator, which encompasses a capillary. After the incubator, the sample is guided into a further mixing chamber, where a reagent is again added via a valve and a pump. After passing through yet another capillary, the sample reaches into a measuring cell, where it is measured by fluorescence imaging. However, on the one hand, the described device cannot attain the required sensitivity for fulfilling the demands on potable water. On the other hand, the consumption of reagents is relatively high due to the continuous operating method, whereby considerable costs are to be expected during operation.

In the event that low concentrations of germs are to be detected in potable water, for example, samples are thus still taken, brought to a laboratory, where germs, which may be present, are detected after incubation on a culture medium.

The demand for an automated device with a high detection sensitivity thus still remains and the invention has made it its object to create such a device, wherein the availability of a filter is assumed, because it is the opinion of the inventors that the desired detection sensitivity can thus be attained in a relatively simple manner and that established reagents can be used. However, the use of a filter does not have the goal of eliminating particles or bacteria for the purpose of obtaining a cleaned solution, such as it is often used in biotechnology, for example, but the goal is a concentration of the bacteria for the purpose of obtaining the required sensitivity in response to a subsequent measuring.

This object is solved by means of a device of the aforementioned type, in the case of which the reactor encompasses a reactor chamber according to the invention and a filtrate chamber, which is separated from said reactor chamber by means of a filter, wherein the at least one water feed line as well as the at least one reagent feed line empty into the reactor chamber and the at least one water discharge line leads out of the filtrate chamber, and wherein the controller is set up to use the pump/valve means to lead a predefinable quantity of water into the reactor chamber and through the filter as well as to introduce a predefinable quantity of reagent into the reactor chamber.

Thanks to the invention, a device is created, which provides for an automated measuring over longer periods of time and which is versatile thanks to its design, so that there is no limitation to certain germs, detection methods or quality of the water, which is to be analyzed, for example.

In a design, which can be realized in a particularly advantageous manner, provision is made for the measuring device to be set up to measure downstream from the filtrate chamber.

To increase the sensitivity, it may be advantageous for a concentration unit to be arranged upstream of the measuring device. It has thereby proven to be particularly effective when the concentration unit operates according to the principle of the chromatographic separation.

The flexibility of the device can be increased in that the measuring device is set up to measure in the reactor chamber and/or to measure in the filtrate chamber.

It is furthermore advisable in many cases when at least the reactor encompasses a heater for the purpose of creating reproducible conditions for the biological/chemical operations.

For a controlled operation of the processes running in the device, it is advantageous when provision is made for a pressure measuring device for the pressure in the water feed line to the reactor chamber.

In the event that a stirring means is provided in the reactor chamber, an even mixing of the reacting substances is ensured.

Provision can furthermore be made for the controller to be set up to reverse the flow of the water through the reactor by means of the pump/valve means. In doing so, measuring can be carried out in the backflow on the one hand, whereby the dilution, which occurs in some cases due to the passing through the filter and a signal reduction connected thereto do not occur, and, on the other hand, the cleaning of the apparatus can thus be facilitated.

Under certain breeding and/or measuring conditions, it may furthermore be sensible when the controller is set up to use the pump/valve means to detect the flow of the water through the reactor in a circle.

Due to the fact that the obtained measuring value should advantageously refer to a certain volume, it is advantageous when the controller is set up to detect and/or predefine the measurement volume conveyed via the pump.

In terms of a largely automatable operation, it is advisable for the filter to be replaceable in the reactor. An advantageous development is thereby characterized in that provision is made for a filter change panel comprising at least two filter cartridges, which, while being sealed from the reactor housing, can be displaced in such a manner, that one filter cartridge as effective filter in each case separates reactor and filtrate chamber or that a drive, which is controlled by the controller, is assigned to the filter change panel, respectively.

Due to the fact that air or gas bubbles can be created for different reasons in the reactor or in the cycle thereof, respectively, and can lead to an interference of the measuring process, it is advisable to remove them from the reactor.

In practice, it has thereby proven to be particularly advantageous when the filter is embodied so as to be substantially plane and is sloped against the horizontal in such a manner that gas bubbles in the reactor chamber can sweep upwards across the filter surface. It is thereby particularly advantageous when the filtrate chamber encompasses discharge line openings for discharging the water into a first and a second water discharge line, wherein the discharge line opening of the first water discharge line is arranged at the highest point of the filtrate chamber and the discharge line opening of the second water discharge line, which supplies the water to the measuring device, is arranged in an axis of symmetry of the reactor, which runs substantially normally to the filter plane. In response to discharging the water at the highest point of the filtrate chamber, gas and air bubbles which are present and which sweep upwards via the filter, which slopes against the horizontal, and which pass the filter, can effectively escape via the discharge line opening of the first water discharge line. In response to the discharge of the water, which is to be supplied in the measuring direction, out of the filtration chamber via the discharge line opening of the second water discharge line, which is located in the axis of symmetry of the reactor, which runs substantially normally to the filter plane, mixing effects and an associated signal reduction can be maintained to be small.

At least for the reactor chamber, provision can furthermore be made for a ventilation line and for a ventilation valve for the purpose of removing air or gas bubbles out of the reactor. In the event that a filter change panel is available, the solution lends itself for the filter change panel to encompass a ventilation recess, which releases a connection between reactor and/or filtrate chamber and a ventilation line leading to the outside in a defined displacement position of the panel.

A development, which encompasses a cleaning unit and in the case of which, by means of controlling the pump/valve means, the controller is set up to guide cleaning fluids through the lines and units of the device in at least one cleaning cycle, contributes to ensure an automated, virtually continuous operation.

The invention including further advantages is illustrated below by means of exemplary embodiments in the drawing.

Figure 2:
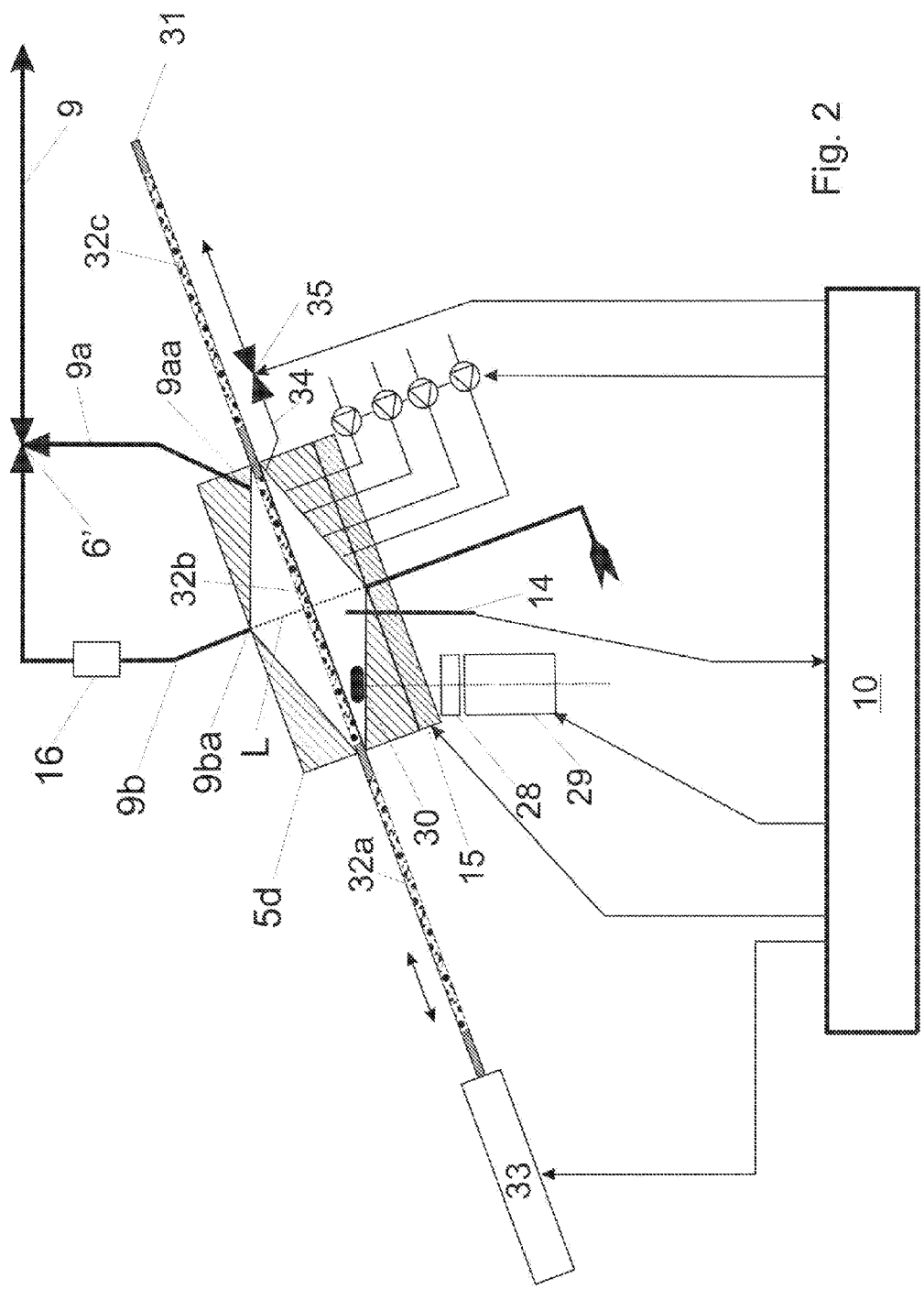
Figure 5:
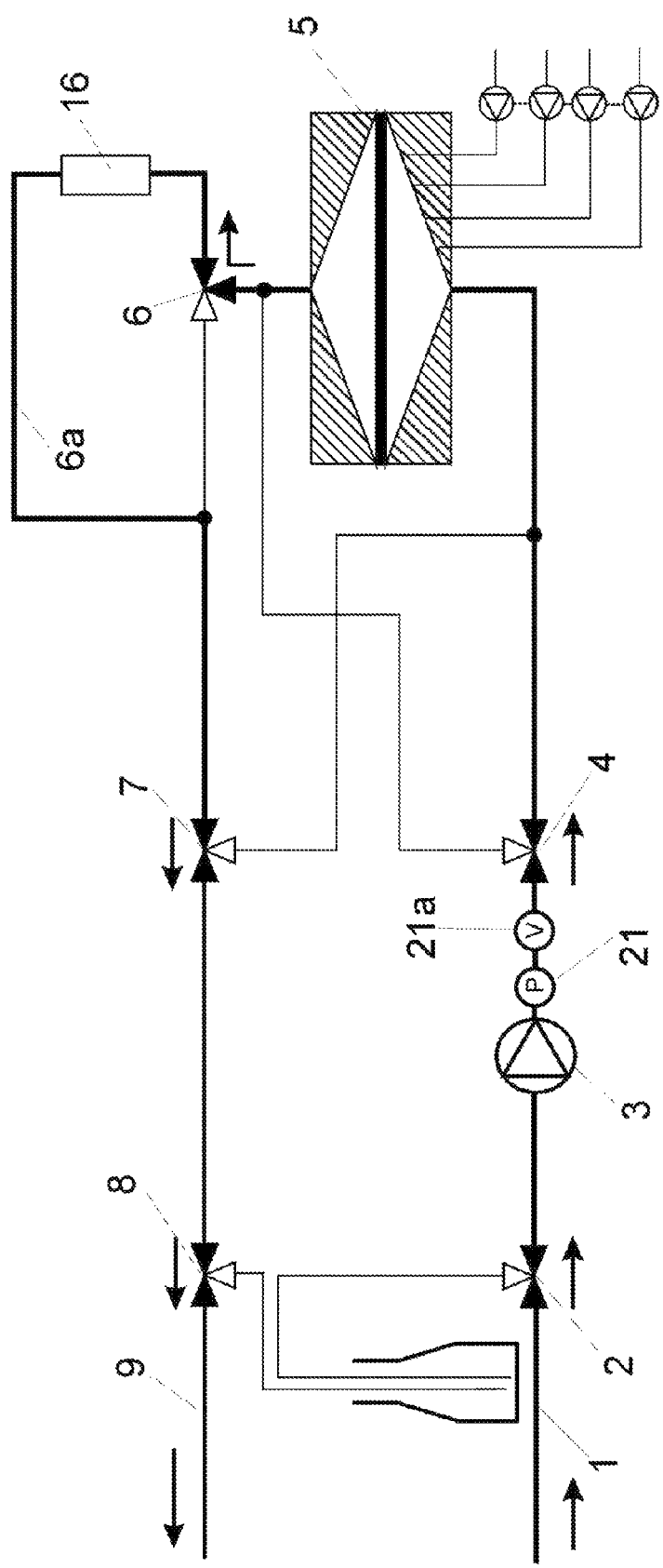
Figure 6:
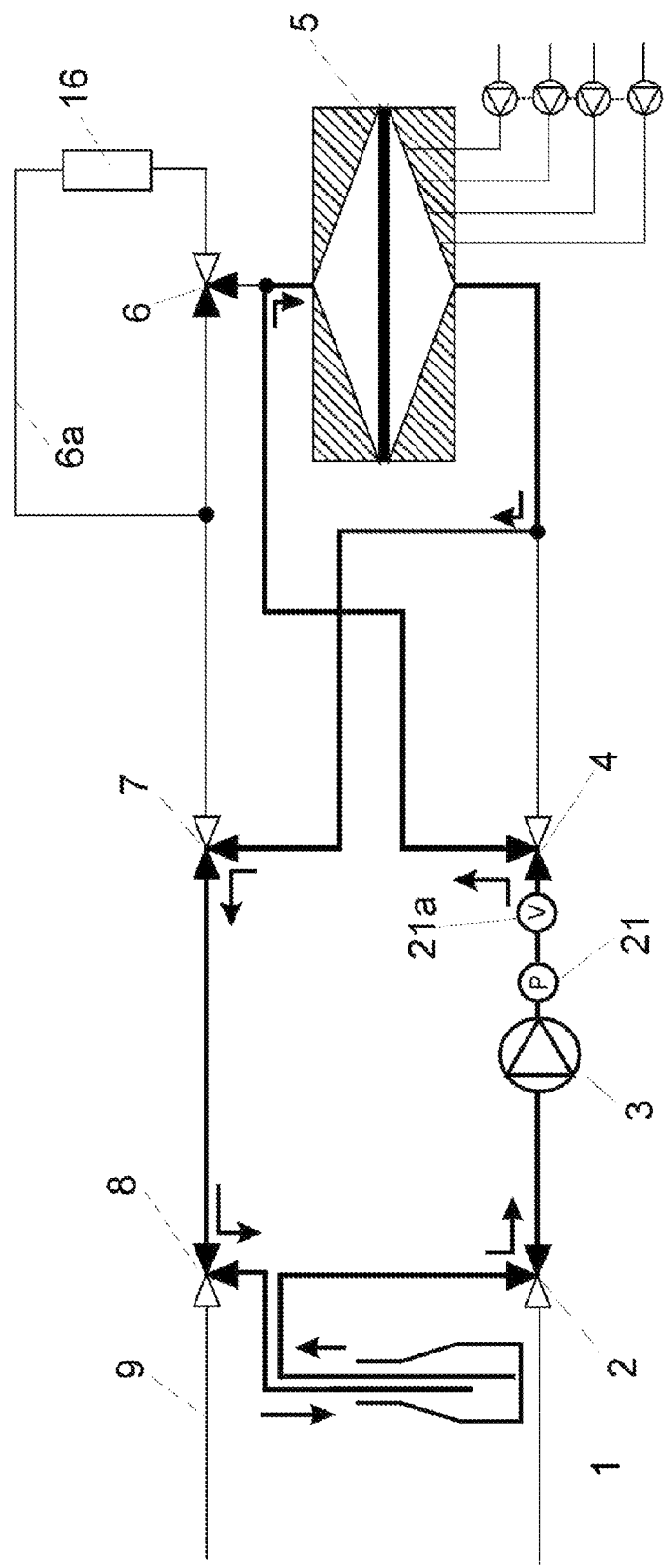
Figure 7:
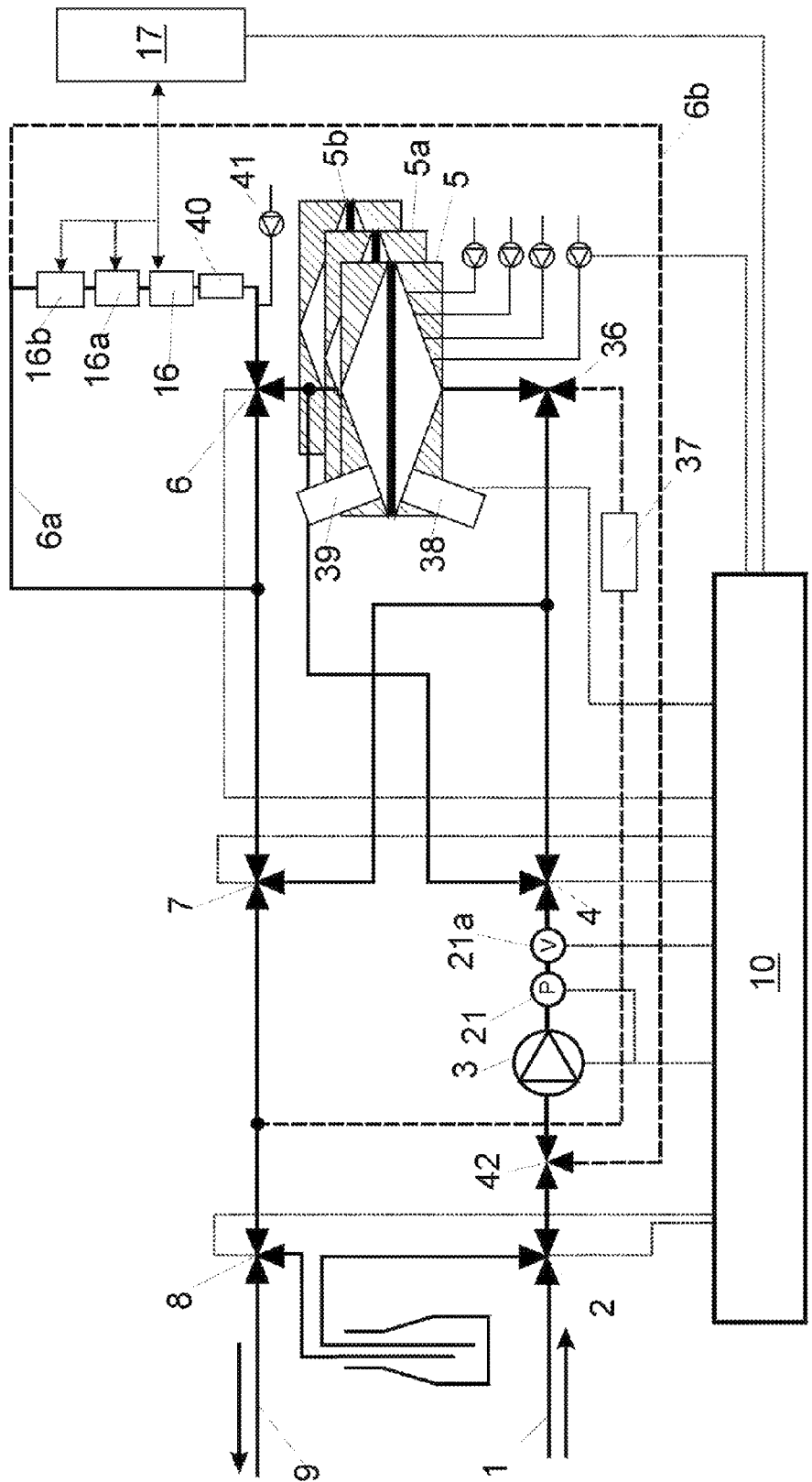

FIG. 1 shows a first embodiment of the invention in a schematic block illustration, FIG. 2 shows a detail of an embodiment according to the invention in an enlarged illustration, FIGS. 3 to 6 show different flow paths during the operation in illustrations according to FIG. 1, wherein, however, portions which are insignificant for the explanation, have been omitted and FIG. 7 shows an embodiment of the invention with expanded functionalities in an illustration, which is similar to FIG. 1.

According to FIG. 1, the water to be analyzed—see above with reference to the definition of "water"—is guided to a reactor 5 via a water feed line 1, a first 3-way valve 2, a pump 3 and a second 3-way valve 4, and is discharged again from there via a water discharge line 9 via a third 3-way valve 6, a fourth 3-way valve 7 and a fifth 3-way valve 8.

All of the 3-way valves are controlled by a central controller 10 or can be operated by it, respectively, wherein it should be clear that the cycle described just now represents only one of several possibilities in response to certain positions of the 3-way valves. It is appropriate that the controller 10 is also set up for a central data acquisition and for a data output.

The reactor 5 has a reactor chamber 11 and a filtrate chamber 13, which is located thereabove herein and which is separated by means of a filter 12. The temperature within the reactor can be detected by means of a temperature sensor 14 and corresponding information can be forwarded to the controller 10. On the other hand, the reactor 5 can be heated by means of a heater 15, which is controlled via the controller, advantageously based on the information of the temperature sensor 14.

In the measuring branch 6a, which starts at the third 3-way valve 6, a measuring device 16, which is connected to a periphery unit 17 for this measuring device, is arranged, wherein, on the other hand, the latter can communicate with the controller 10.

Reagents from storage containers 20a, 20b, 20c and 20d can be introduced into the reactor chamber 11 via reagent feed lines 18a, 18b, 18c and 18d and via metering valves 19a, 19b, 19c and 19d, which are assigned thereto and which can be controlled by the controller 10.

A pressure measuring device 21, which forwards the value of the current pressure to the controller 10, is arranged between the pump 3 and the second 3-way valve 4, so that said controller 10 can maintain the pressure at a predefinable value, for example via the capacity of the pump 3.

A branch 22 or 23, respectively leads from the first 3-way valve 2 or the fifth 3-way valve 8, respectively, to a cleaning device 24, which in the illustrated exemplary embodiment includes at least one receptacle 25 for a cleaning fluid, wherein a limitation to liquid cleaning agents does not take place here and other possibilities, such as the generation of ozone, e.g., can be used for cleaning purposes.

A transverse line 26 connects the output of the filter chamber 13 to the second 3-way valve 4, a transverse line 27 connects the input of the reactor chamber 11 to the fourth 3-way valve 7.

Prior to discussing the function or the different operating modes of a device according to the invention, further details shall be explained by means of FIG. 2, in which the same reference numerals are used for the same parts as in FIG. 1 and parts, which have already been explained in FIG. 1, are omitted.

FIG. 2 shows a reactor 5d, which is inclined at an angle with reference to the horizontal. Due to the incline of the reactor 5d, the filter panel 31 is also inclined.

So as to be able to maintain a certain fluid motion in the reactor chamber 11, provision is made here for a magnetic stirrer 28, which encompasses a motor 29 and a stirring magnet 30 in the interior of the chamber 11. The motor 29, in turn, is controlled by the central controller 10. It goes without saying that other technologies can also be used so as to maintain a motion in the reactor chamber 11, provided that this motion is desired. The incline of the reactor 5d results in a substantially horizontal surface in the reactor chamber 11 for the stirring magnet 30. In the case of a suitable arrangement, the force of gravity holds the stirring magnet 30 in the lowest position due to the geometry of the reactor chamber.

So as to be able to automatically replace a used or damaged filter, the device has a filter change panel 31 comprising three filter cartridges 32a, 32b and 32c. These filter cartridges can be standard ceramic filters, for example. A drive 33 controlled by the controller 10 can now displace the filter change panel 31, wherein said panel is sealed from the reactor housing, so that a different filter cartridge separates the reactor chamber from the filter chamber in each case as an effective filter. In the shown position, the filter cartridge 32b is in effect.

Air or gas bubbles, which are stopped by the filter and which can have an interfering effect mainly in the reactor chamber 11, can form for different reasons and at different locations in the conduit. Due to the incline of the reactor 5d and of the filter panel 31 at an angle, air or gas bubbles, which may be present in the reactor chamber 11 can sweep upwards along the filter surface, can be pressed through the filter 12 into the filtrate chamber 13 and can be discharged. In the case of the shown embodiment, two water discharge lines 9a and 9b lead out of the filtrate chamber 13 of the reactor 5d. The discharge line opening 9aa of the first water discharge line 9a is substantially located at the highest location of the filtrate chamber 13 and serves the purpose of discharging the water out of the reactor 5d during the filtration process. Air bubbles, which are present and which sweep upwards in the reactor chamber along the filter surface and which pass the filter 12, can escape via the first water discharge line 9a by means of this arrangement. The discharge line opening 9ba of the second water discharge line 9b, via which the water is supplied to the measuring device 16, is arranged in the axis of symmetry L of the reactor 5d. The axis of symmetry L of the reactor 5d thereby runs substantially normally to the filter surface. This arrangement has the advantage that a discrimination of the reaction solution—due to different paths from the filter surface to the discharge line opening 9ba of the second water discharge line 9b—does not take place in response to the measuring process, in the case of which the solution to be measured is guided from the reactor chamber 11 through the filter 12 into the filtrate chamber 13 and from there via the second water discharge line 9b into the measuring device 16, and that mixing effects and an associated signal reduction are kept small. The water discharge lines 9a and 9b empty into a water discharge line 9 via a 3-way valve 6'.

Additionally, air or gas bubbles can be removed via a ventilation of the reactor 5d. For the latter, the reactor chamber 11 can thus be provided with a vent pipe 34 and with a vent valve 35, so that a venting can be carried out as needed or at certain times in the process flow. It also makes sense here, when the filter, which is typically embodied so as to be plane, is inclined against the horizontal in such a manner that gas bubbles in the reactor chamber 11 sweep upwards across the filter surface and are thus able to reach the inlet of said vent pipe 34.

In the following, the operation and the function of a device according to the invention will be explained with reference to FIGS. 3 to 6.

Figure 3:
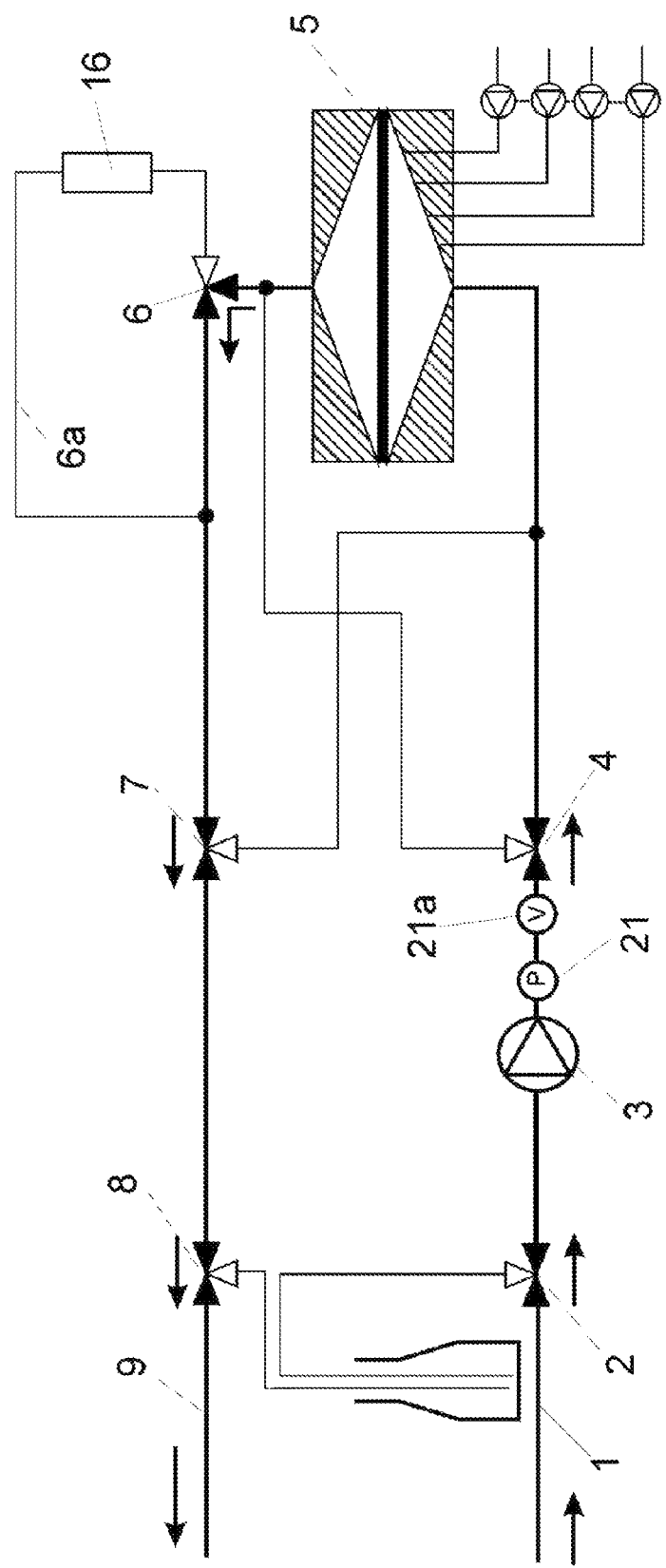
Figure 4:
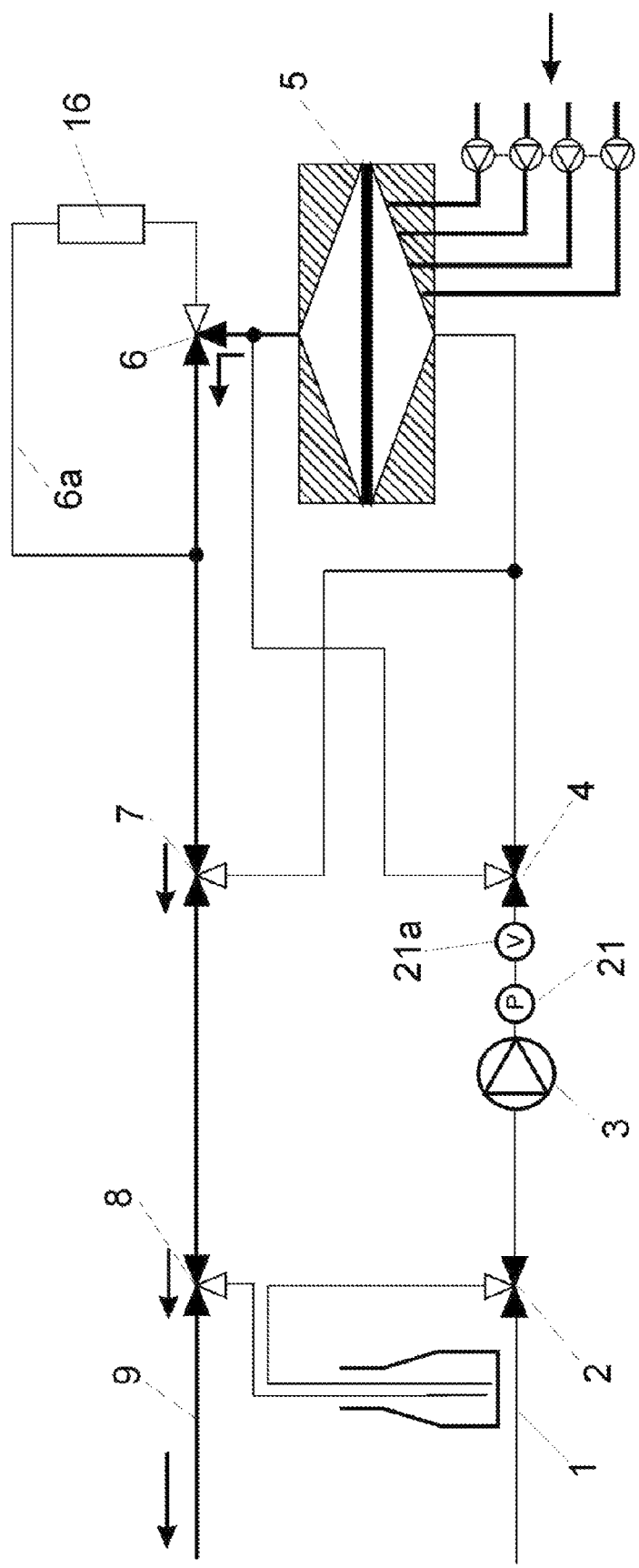

FIG. 3 shows the valve positions and the corresponding flow in the operating mode "filtration". The sample is thereby constantly sucked in via the water feed line 1 by means of the pump 3 and is guided up to the discharge line 9 through the reactor chamber 11, the filter 12 and the filtrate chamber 13. So as to provide a reference of the later obtained measuring value to a volume, e.g. the number of germs per 100 ml, the filtered volume of water samples is measured or is supplied in a dosed manner, respectively. For this, the rotations of the pump 3 can be detected, for example, or a flow measuring device 21a can be used for detecting the volume conveyed through the pump 3. This flow measuring device 21a supplies corresponding information to the controller 10 and said controller can then turn off the pump 3 after reaching a certain conveyed volume or it can close valves. Microbial germs are held back at the filter 12. The operating mode "filtration" is followed by the operating mode "metering and incubation" according to FIG. 4, during the course of which reagents from the storage containers 20a, 20b, 20c and 20d are initially introduced into the reactor chamber 11 via the reagent feed lines 18a, 18b, 18c and 18d and via metering valves 19a, 19b, 19c and 19d, which are assigned to said reagent feed lines and which can be controlled by the controller 10. The volume displaced thereby leaves the reactor via the filter, so that the volume in the reactor chamber remains constant. The adding of the reagents can take place selectively at different times of the incubation. The heater 15 as well as the magnetic stirrer 28, which are regulated via the temperature sensor 14 and via the controller 10, ensure optimal reaction conditions.

The following measuring step takes place in the operating mode "measuring" according to FIG. 5. The pump 3 is turned on again and water flowing via the feed line 1 pushes the solution to be measured, which is located in the reactor chamber 11, through the filter 12 via the filtrate chamber 13 and from here via the third 3-way valve 6 into a measuring cell of the measuring device 16. The measuring value, which can be output via the periphery unit 17 and/or via the controller 10, describes the concentration of the analytes in the reactor chamber at the end of the incubation. Alternatives of the measuring possibilities and measuring locations will be described further below in context with FIG. 7.

The detection of *Escherichia coli* (*E. coli*) is given herein as example for an analytical method. *E. coli* is an indicator for fecal contamination and is routinely used worldwide for monitoring potable water, among other things.

A defined volume of samples is filtered out by means of the pump via the filter in the reactor chamber. Buffer solution and substrate solution are added into this volume of the reactor chamber comprising the enhanced bacteria. The buffer solution provides ideal conditions for the enzymatic reaction, the substrate solution contains a substrate, which can be converted selectively by means of a certain enzyme of *E. coli*. The established substrate in context with *E. coli* is 4-methylumbelliferyl-β-D-glucuronide, which is separated by the enzyme β-D-glucuronidase, which is typical for *E. coli* and which thus releases the highly fluorescing 4-methylumbelliferon, which is measured by fluorescence imaging.

A cultivation of the bacteria can be omitted due to the high sensitivity of the device according to the invention, which is attained by combining enriched and sensitive measuring. The conditions can thus also be specifically adjusted to those of the β-glucuronidase in the course of the incubation.

The volume of the reactor chamber is measured in the measuring cell 16 after a corresponding incubation, which, depending on the expected amount of *E. coli*, can be in the range of 1-6 hours. The attained signal is a measure for the number of the *E. coli* in the reactor chamber; the content of germs per units of volume can be computed by means of the known, filtered sample volume.

In the alternative, a signal flow can be picked up over the time of the incubation, when the measuring cell or measuring device, respectively, is used in the reactor chamber.

The detection of *E. coli* by means of detecting selective enzymatic activity, however, is only one of several applications of the instant invention. By means of the modifications and combinations, which will be described below, it is also possible, e.g., i.) to stain and measure germs in general, wherein ii.) a general cell staining (e.g. living staining) or iii.) a selective cell staining e.g. with antibodies can be carried out or also iv.) a method using the selective cultivation with subsequent measuring.

Several steps can run in the operating mode "backflushing and cleaning", see FIG. 6, wherein a repeated execution and/or repetition of individual steps is possible.

The cleaning device 24, which is controlled by means of the controller 10, thereby removes this cleaning agent, if applicable also several cleaning agents, from the receptacle 25 for the cleaning fluid, e.g. chlorine water. The sample path is flushed as in the operating mode "filtration". The reactor can furthermore also be flushed only with water and a backflush of the reactor can also take place by means of a cleaning agent. The measuring branch 6a can also be included in the cleaning and/or back-flush. The entire cleaning operation can run automatically and is adapted to the respectively conditions at hand, such as to the type of the microorganisms, reagents and cleaning agents, which are to be detected, so that the device is available for measuring a new sample after the cleaning process has ended.

As compared to the embodiment according to FIG. 1, the embodiment shown in FIG. 7 has several upgrades, e.g. an additional second reactor 5a and a third reactor 5b; some parts, which have already been shown in FIGS. 1 and 2, such as heater and stirring means, have been omitted so as to simplify the illustration.

A sixth 3-way valve 36 upstream of the inlet into the reactor chamber 11 and an additional/alternative measuring device 37 in the backflow.

One further measuring device 38 and 39 can in each case be arranged or provided, respectively, in the or for the reactor chamber 11 and the filtrate chamber 13, respectively, wherein the measuring device 38 is preferred for the reactor chamber 11. Further measuring devices 16a and 16b can be arranged in the measuring branch 6a, connected downstream from the measuring device 16. In the alternative, these measuring devices can also be connected in parallel.

A seventh 3-way valve 42 between the first 3-way valve 2 and the pump 3 and the measuring branch 6b serve the purpose of recirculating the measuring solution during the incubation. A concentration unit 40 is added upstream of the measuring devices 16, 16a, 16b for the purpose of increasing the sensitivity of the measuring. It can be based on chromatography, wherein an eluent can be supplied via a controlled pump 41 for removing the enhanced analytes.

LIST OF REFERENCE NUMERALS 1 water feed line
2 first 3-way valve
3 pump
4 second 3-way valve
5 reactor
5a second reactor
5b third reactor
5d reactor comprising two water discharge lines
6 third 3-way valve
6' third 3-way valve according to FIG. 2
6a measuring branch
6b measuring branch
7 fourth 3-way valve
8 fifth 3-way valve
9 water discharge line
9a first water discharge line
9aa discharge line opening of the first water discharge line
9b second water discharge line
9ba discharge line opening of the second water discharge line
10 central controller
11 reactor chamber
12 filter
13 filtrate chamber
14 temperature sensor
15 heater
16 measuring device
16a,b measuring devices
17 periphery unit
18a-d reagent feed lines
19a-d metering valves
20a-d storage containers
21 pressure measuring device
21a flow measuring device
22 branch
23 branch
24 cleaning device
25 receptacle for a fluid
26 transverse line
27 transverse line
28 magnetic stirrer
29 motor
30 stirring magnet
31 filter change panel
32a,b,c filter cartridges
33 drive
34 vent pipe
35 vent valve
36 sixth 3-way valve
37 measuring device
38 measuring device
39 measuring device
40 concentration unit
41 pump
42 seventh 3-way valve
L axis of symmetry of the reactor 5d

The invention claimed is:

1. A device for monitoring water, comprising:
a reactor, the reactor comprising a reactor chamber, a filtrate chamber, and a filter, the filtrate chamber being separated from the reactor chamber by the filter, the filter being substantially planar and inclined relative to horizontal in such a manner that gas bubbles in the reactor chamber can sweep upwards across a surface of the filter;
at least one water feed line connected to the reactor chamber, the at least one water feed line being operatively configured to introduce the water to be monitored into the reactor chamber; the at least one water feed line comprising at least one pump or valve
at least one water discharge line connected to the filtrate chamber, the at least one water discharge line comprising at least one valve;
at least one reagent feed line, the at least one reagent feed line being connected to the reactor chamber and at least one reagent metering device;
at least one measuring device for detecting the presence of microorganisms and/or the metabolic products thereof; and
a controller, the controller being operatively configured to control the at least one pump or valve in the at least one water feed line and the at least one valve in the at least one water discharge line to direct a predefinable quantity of water into the reactor chamber and through the filter, the controller being operatively configured to control the at least one reagent metering device to introduce a predefinable quantity of a reagent into the reactor chamber.

2. The device according to claim 1, characterized in that the at least one measuring device is operatively configured to measure downstream from the filtrate chamber.

3. The device according to claim 2, further comprising a concentration unit that is arranged upstream from the at least one measuring device.

4. The device according to claim 3, characterized in that the concentration unit operates according to the principle of chromatographic separation.

5. The device according to claim 1, characterized in that the at least one measuring device is operatively configured to measure in the reactor chamber.

6. The device according to claim 1, characterized in that the at least one measuring device is operatively configured to measure in the filtrate chamber.

7. The device according to claim 1, characterized in that the reactor encompasses a heater.

8. The device according to claim 1, further comprising a pressure measuring device in the at least one water feed line.

9. The device according to claim 1, further comprising a stirrer located in the reactor chamber.

10. The device according to claim 1, characterized in that the controller is operatively configured to communicate with the at least one pump or valve in the at least one water feed line and the at least one valve in the at least one water discharge line in order to guide the flow of the water through the reactor in a circle.

11. The device according to claim 1, characterized in that the controller is operatively configured to detect and/or to predefine the measurement volume conveyed via the at least one pump in the at least one water feed line.

12. The device according to claim 11, further comprising a flow measuring device arranged downstream from the at least one pump in the at least one water feed line.

13. The device according to claim 1, characterized in that the filter is replaceable.

14. The device according to claim 1, further comprising a filter change panel comprising at least two filter cartridges, the filter change panel being displaceable, wherein when the filter change panel is displaced, the filter that separates the reactor chamber from the filtrate chamber is alternated between a first filter cartridge of the least two filter cartridges and a second filter cartridge of the at least two filter cartridges.

15. The device according to claim 14, further comprising a drive controlled by the controller, wherein the drive is used to displace the filter change panel.

16. The device according to claim 14, characterized in that the filter change panel encompasses a ventilation recess, which releases a connection between the reactor and/or filtrate chamber and a ventilation line in a defined displacement position of the filter change panel.

17. The device according to claim 1, characterized in that the filtrate chamber encompasses discharge line openings for discharging the water into a first water discharge line and a second water discharge line, wherein the discharge line opening of the first water discharge line is arranged at a highest point of the filtrate chamber and the discharge line opening of the second water discharge line, which supplies the water to the at least one measuring device, is arranged in an axis of symmetry of the reactor, which runs substantially normally to a plane of the filter.

18. The device according to claim 1, characterized in that the reactor chamber comprises a vent pipe and a vent valve connected thereto.

19. The device according to claim 18, further comprising a filter change panel encompassing a ventilation recess, which releases a connection between the reactor and/or filtrate chamber and a ventilation line in a defined displacement position of the filter change panel.

20. A device for monitoring water, comprising:
a reactor, the reactor comprising a reactor chamber, a filtrate chamber, a filter, and a filter change panel, the reactor chamber comprising a vent pipe and a vent valve connected thereto, the filtrate chamber being separated from the reactor chamber by the filter, the filter change panel comprising at least two filter cartridges, the filter change panel being displaceable, wherein when the filter change panel is displaced, the filter that separates the reactor chamber from the filtrate chamber is alternated between a first filter cartridge of the least two filter cartridges and a second filter cartridge of the at least two filter cartridges, the filter change panel encompassing a ventilation recess, which releases a connection between the reactor and/or filtrate chamber and a ventilation line in a defined displacement position of the filter change panel;
at least one water feed line connected to the reactor chamber, the at least one water feed line being operatively configured to introduce the water to be monitored into the reactor chamber; the at least one water feed line comprising at least one pump or valve
at least one water discharge line connected to the filtrate chamber, the at least one water discharge line comprising at least one valve;
at least one reagent feed line, the at least one reagent feed line being connected to the reactor chamber and at least one reagent metering device;
at least one measuring device for detecting the presence of microorganisms and/or the metabolic products thereof; and
a controller, the controller being operatively configured to control the at least one pump or valve in the at least one water feed line and the at least one valve in the at least one water discharge line to direct a predefinable quantity of water into the reactor chamber and through the filter, the controller being operatively configured to control the at least one reagent metering device to introduce a predefinable quantity of a reagent into the reactor chamber.

21. A device for monitoring water, comprising:
a reactor, the reactor comprising a reactor chamber, a filtrate chamber, a filter, and a filter change panel, filtrate chamber being separated from the reactor chamber by the filter, the filter being replaceable, the filter change panel comprising at least two filter cartridges, the filter change panel being displaceable, wherein when the filter change panel is displaced, the filter that separates the reactor chamber from the filtrate chamber is alternated between a first filter cartridge of the least two filter cartridges and a second filter cartridge of the at least two filter cartridges;
at least one water feed line connected to the reactor chamber, the at least one water feed line being operatively configured to introduce the water to be monitored into the reactor chamber; the at least one water feed line comprising at least one pump or valve
at least one water discharge line connected to the filtrate chamber, the at least one water discharge line comprising at least one valve;
at least one reagent feed line, the at least one reagent feed line being connected to the reactor chamber and at least one reagent metering device;

at least one measuring device for detecting the presence of microorganisms and/or the metabolic products thereof; and a controller, the controller being operatively configured to control the at least one pump or valve in the at least one water feed line and the at least one valve in the at least one water discharge line to direct a predefinable quantity of water into the reactor chamber and through the filter, the controller being operatively configured to control the at least one reagent metering device to introduce a predefinable quantity of a reagent into the reactor chamber.

\* \* \* \* \*